United States Patent [19]

Anello et al.

[11] 4,377,717
[45] Mar. 22, 1983

[54] METHOD FOR THE PRODUCTION OF PERFLUORO-2-METHYLPENTENE-2

[75] Inventors: Louis G. Anello, Hamburg; Richard F. Sweeney, Elma, both of N.Y.

[73] Assignee: Allied Corporation, Morris Township, Morris County, N.J.

[21] Appl. No.: 330,066

[22] Filed: Dec. 14, 1981

[51] Int. Cl.³ .............................................. C07C 17/26
[52] U.S. Cl. .................................................... 570/172
[58] Field of Search ........................................ 570/172

[56] References Cited

U.S. PATENT DOCUMENTS 2,918,501 12/1959 Brehm et al. ...................... 570/172

Primary Examiner—Charles F. Warren
Assistant Examiner—Joseph A. Boska
Attorney, Agent, or Firm—Jay P. Friedenson

[57] ABSTRACT

Perfluoro-2-methylpentene-2 may be prepared by heating hexafluoropropylene at elevated temperatures in the presence of activated carbon. The activated carbon serves as a catalyst for the dimerization of the hexafluoropropylene.

7 Claims, No Drawings

METHOD FOR THE PRODUCTION OF PERFLUORO-2-METHYLPENTENE-2

DESCRIPTION

1. Technical Field

This invention relates to a method for the production of perfluoro-2-methylpentene-2 which comprises heating hexafluoropropylene at elevated temperatures in the presence of activated carbon.

2. Background of the Invention

Perfluoro-2-methylpentene-2 is a known compound which has been prepared by contacting hexafluoropropylene with catalyst-solvent combinations comprising halides and hydroxides of metals of Group I of the periodic table of elements as catalysts in combination with solvents of the class consisting of N,N-dialkylamides; N,N-diphenylamines and dialkylsulfoxides and certain quaternary ammonium salts as catalysts in combination with solvents of the class consisting of hydrocarbons; N,N-dialkylamines and N,N-dialkylamides. Such prior art reactions have been carried out at temperatures from about 0°–200° C. These preparations are disclosed in U.S. Pat. No. 2,918,501.

Another prior art method for the preparation of perfluoro-2-methylpentene-2 is by the reaction of hexafluoropropylene with CSF at a temperature of about 200° C. under autogenous pressure in the absence of a solvent (R. D. Dresdner, F. N. Tumac and J. A. Young, J. Org. Chem., 30 3524, 1965).

The above described prior art preparations of perfluoro-2-methylpentene-2 are characterized by being liquid phase, batch operations with low conversions and yields.

It is an object of the present invention to provide a novel, gas phase method for the preparation of perfluoro-2-methylpentene-2 which produces such product in high conversions and high yields.

It is another object of this invention to provide a novel method for making perfluoro-2-methylpentene-2 in high yields and conversions in a continuous fashion.

Other objects and advantages of the invention will be apparent from the following description.

SUMMARY OF THE INVENTION

In accordance with the invention, it has been found that activated carbon promotes dimerization of hexafluoropropylene, when heated, by an easily controllable gas phase catalytic procedure in which perfluoro-2-methylpentene-2 is obtained in high conversions and yields. Accordingly, in accordance with the invention perfluoro-2-methylpentene-2 is produced by heating hexafluoropropylene at elevated temperatures in the presence of activated carbon.

DETAILED DESCRIPTION OF THE INVENTION AND OF THE PREFERRED EMBODIMENTS

The process of the invention may easily be carried out by continuously passing perfluoropropylene vapor over activated carbon at elevated temperatures. A tubular reactor constructed of an inert material such as Alundum, nickel, Monel, Inconel or stainless steel may be used. Exit gases may be suitably cooled to trap all products and the products when are fractionally distilled. The products recovered by distillation are unreacted hexafluoropropylene (b.p. −28° C.) and the desired perfluoro-2-methylpentene-2 (b.p. 50.5° C.).

As disclosed in U.S. Pat. No. 2,918,501, perfluoro-2-methylpentene-2 is useful as a solvent and as a reaction medium, particularly where fluorinated solvents are employed and additionally may be employed as a refrigerant.

Any of the well-known activated carbon materials may be used in practice of the invention. Activated carbon is an amorphous form of carbon characterized by high adsorptivity for many gases, vapors and colloidal solids. The carbon is obtained by the destructive distillation of wood, nut shells, animal bones or other carbonaceous material. It is "activiated" by heating to 800°–900° C. with steam or carbon dioxide which results in a porous internal structure. (*The Condensed Chemical Dictionary*, 9th Ed., p. 163).

A variety of activated carbons are commercially available under trademarks and grades such as Columbia MBV, Columbia MBQ, Columbia JXC, Columbia SBV, Barneby Cheney NB and Darco. The source, grade or form of the activated carbon is not critical to the invention, however, the preferred form is granules to facilitate use in tubular reactors. The size of the granules is not critical, but where tubular reactors are employed, it is desirable to employ activated carbon granules of an average mesh size (U.S. Standard) between about 1/25 and ¼ of the reactor diameter. Most preferred conditions are those in which a reactor is substantially completely filled with granules of an average mesh size of about 1/6–1/10 of the reactor diameter.

The temperature in the reaction zone needs to be elevated but operable temperatures lie over a wide range. The preferred temperature range is between about 250°–500° C. Still preferred are reaction temperatures between about 350°–450° C. and most preferred are reaction temperatures between about 375°–425° C.

Contact or retention time of the perfluoropropylene vapor starting material with the activated carbon catalyst is not critical since appreciable conversions are obtained even at very short contact times, for example in the order of about 0.5 second. Best results, however, are obtained with retention times in the range of about 1–60 seconds although much longer retention times such as five minutes or more can be employed without deleterious result.

The process is most conveniently conducted at atmospheric presure. Higher or lower pressures may be employed, however, without any particular advantage.

The following examples are illustrative of the practice of the invention. Parts and percentages are by weight and mesh sizes are U.S. Standard.

EXAMPLE I 145 ml of Columbia MBV activated carbon granules (4–6 mesh) were charged to a one inch I.D. Monel tubular reactor, 27 inches long, heated externally over about 24 inches of its length by an electric furnace provided with an automatic temperature control. Columbia MBV activated carbon is available from Union Carbide Corporation. It is a form of activated charcoal derived from bituminous coal. Activated carbon granules have an average mesh size of about 1/6.6 of the reactor diameter. During a period of 3½ hours, 438 grams (2.91 moles) of hexafluoropropylene were passed over the activated carbon at a temperature of 410° to 420° C. with a retention time of 13 seconds. The exit products from the reactor were passed into a dry-ice acetone cold trap. Fractional distillation of the 408 grams of cold trap product effected recovery of 235 grams (1.57 moles) of unreacted hexafluoropropylene (b.p. −28° C.) and 130 grams (0.43 mole) of perfluoro-2-methylpentene-2 (b.p. 50.5° C.). Thus, of the starting material fed, 29.6% was converted to perfluoro-2-methylpentene-2. The yield, based on starting material consumed, was 64.5%. The NMR and IR of the recovered perfluoro-2-methylpentene-2 product were consistent with the expected structure.

EXAMPLE II

Following the procedure of Example I and with the same apparatus, 553 grams (3.7 moles) of hexafluoropropylene were passed over 145 ml of Columbia SBV activated carbon granules (4–6 mesh) at a temperature of 425° C. and with a retention time of about 15 seconds. Columbia SBV activated carbon is available from Union Carbide Corporation. It is a form of activated carbon derived from coconut shells. The activated carbon granules have an average mesh size of about 1/6.6 of the reactor diamger. Fractional distillation of the 547 grams of the cold trap product effective recovery of 322 grams (2.15 moles) of hexafluoropropylene and 188 grams (0.62 mole) of perfluoro-2-methylpentene-2. Thus, of the hexafluoropropylene starting material fed, 33.5% was converted to perfluoro-2-methylpentene-2. The yield based on starting material consumed was about 80%. The NMR and IR of the recovered perfluoro-2-methylpentene-2 product were consistent with the expected structure.

EXAMPLE III

Following the procedure of Example I and with the same apparatus, 297 grams (1.98 moles) of hexafluoropropylene were passed over 145 ml of Columbia JXC activated carbon granules (4–6 mesh) at a temperature of 425° C. and with a retention time of 11 seconds. Columbia JXC activated carbon is available from Union Carbide Corporation. It is a form of activated carbon derived from petroleum residue. The activated carbon granules have an average mesh size of about 1/6.6 of the reactor diameter. Distillation of the 269 grams of the cold trap product effected recovery of 166.4 grams (1.10 moles) of hexafluoropropylene and 96.8 grams (0.32 mole) of perfluoro-2-methylpentene-2. Thus, of the starting material fed, 32.4% was converted to perfluoro-2-methylpentene-2. The yield based on the starting material consumed was about 73%. The NMR and IR of the recovered product were consistent with the expected structure.

EXAMPLES IV–IX

The procedure of Example I is repeated in the same apparatus excepting that catalyst and conditions are varied as shown in the following table. In all cases, perfluoro-2-methylpentene-2 product is obtained in good yields and with good conversions.

| Example | Catalyst | Catalyst Reactor Diameter Ratio | Temperature (°C.) |
| --- | --- | --- | --- |
| IV | Darco | 1/6 | 250 |
| V | Columbia MBQ* | 1/10 | 500 |
| VI | Columbia JXC | 1/4 | 350 |
| VII | Barneby Cheney NB** | 1/25 | 450 |
| VIII | Darco | 1/6 | 375 |
| IX | Columbia SBV | 1/10 | 425 |

*Derived from bituminous coal.
**Derived from hardwood charcoal.

We claim:
1. A method for the production of perfluoro-2-methylpentene-2 which comprises heating hexafluoropropylene at elevated temperatures in the presence of activated carbon.
2. A method according to claim 1 in which the activated carbon comprises granules and in which the elevated temperatures are between about 250°–500° C.
3. A method according to claim 2 in which the elevated temperatures are between about 350°–450° C.
4. A method according to claim 2 in which the elevated temperatures are between about 375°–425° C.
5. A method according to claim 2 in which the activated carbon comprises granules of an average mesh size between about 1/25 and ¼ of the diameter of the reactor employed.
6. A method according to claim 2 in which the activated carbon comprises granules of an average mesh size between about 1/6 and 1/10 of the diameter of the reactor employed.
7. A method according to claim 6 in which the elevated temperatures are between about 375°–425° C.

* * * * *